(12) United States Patent
Brown et al.

(10) Patent No.: US 10,905,409 B2
(45) Date of Patent: *Feb. 2, 2021

(54) TISSUE REPAIR ASSEMBLY

(71) Applicant: ArthroCare Corporation, Austin, TX (US)

(72) Inventors: Treg Brown, Carbondale, IL (US); Nathaniel Cohen, Los Gatos, CA (US); Robert Fernandez, Campbell, CA (US); Richard D'Elia, San Mateo, CA (US); Christopher D'Elia, San Mateo, CA (US); Annette Branger, San Carlos, CA (US); Steve Golden, Menlo Park, CA (US); Marnette Atkinson, Menlo Park, CA (US); Stewart Kume, Menlo Park, CA (US)

(73) Assignee: ArthroCare Corporation, Austin, TX (US)

( * ) Notice: Subject to any disclaimer, the term of this patent is extended or adjusted under 35 U.S.C. 154(b) by 277 days.

This patent is subject to a terminal disclaimer.

(21) Appl. No.: 15/937,307

(22) Filed: Mar. 27, 2018

(65) Prior Publication Data

US 2018/0214143 A1 Aug. 2, 2018

Related U.S. Application Data

(63) Continuation of application No. 13/677,112, filed on Nov. 14, 2012, now Pat. No. 9,962,149.

(Continued)

(51) Int. Cl.
*A61B 17/04* (2006.01)
*A61B 90/00* (2016.01)

(52) U.S. Cl.
CPC .......... *A61B 17/04* (2013.01); *A61B 17/0401* (2013.01); *A61B 2017/0403* (2013.01);
(Continued)

(58) Field of Classification Search
CPC ................ A61B 17/04; A61B 17/0401; A61B 2017/0409; A61B 2017/0464
See application file for complete search history.

(56) References Cited

U.S. PATENT DOCUMENTS

| 2004/0012245 A1 | 6/2004 | Saadt et al. |
| 2004/0122456 A1 | 6/2004 | Saadat et al. |

(Continued)

FOREIGN PATENT DOCUMENTS

| EP | 2430984 | 3/2012 |
| WO | 2012151592 | 11/2012 |
| WO | 2016205351 | 12/2016 |

OTHER PUBLICATIONS

AU Office Action for AU2017210662 dated Mar. 29, 2018, 5 pages.
(Continued)

*Primary Examiner* — Sarah A Simpson
(74) *Attorney, Agent, or Firm* — Norman F. Hainer, Jr.

(57) ABSTRACT

A tissue repair assembly for attachment of tissue to bone or tissue to tissue having a soft anchoring implant 100 with a length of suture 120 there through for tensioning the implant and facilitating attachment of other tissue. The implant 100 is a soft, flexible, three-dimensional structure that has a resident volume 200. An inserter tube 310 facilitates the placement of the implant 100 into bone or adjacent soft tissue where it may be deployed. Upon deployment, the soft anchoring implant 100 shortens axially and expands radially, achieving a larger diameter than the hole through which it was placed, thus resisting pull out.

20 Claims, 11 Drawing Sheets

Related U.S. Application Data

(60) Provisional application No. 61/559,672, filed on Nov. 14, 2011.

(52) U.S. Cl.
CPC . *A61B 2017/045* (2013.01); *A61B 2017/0406* (2013.01); *A61B 2017/0409* (2013.01); *A61B 2017/0414* (2013.01); *A61B 2017/0417* (2013.01); *A61B 2017/0445* (2013.01); *A61B 2017/0446* (2013.01); *A61B 2017/0458* (2013.01); *A61B 2017/0459* (2013.01); *A61B 2017/0464* (2013.01); *A61B 2090/033* (2016.02); *F04C 2270/0421* (2013.01)

(56) References Cited

U.S. PATENT DOCUMENTS

| | | | | |
|---|---|---|---|---|
| 2006/0178683 | A1* | 8/2006 | Shimoji | A61B 17/07207 606/151 |
| 2007/0010857 | A1 | 1/2007 | Sugimoto et al. | |
| 2009/0062847 | A1 | 3/2009 | Ken | |
| 2010/0203155 | A1* | 8/2010 | Wei | A61B 17/8825 424/549 |
| 2011/0022084 | A1 | 4/2011 | Kaiser et al. | |
| 2011/0098727 | A1 | 4/2011 | Kaiser et al. | |
| 2012/0239085 | A1* | 9/2012 | Schlotterback | A61B 17/0401 606/228 |

OTHER PUBLICATIONS

CN Office Action for CN App No. 201280067035.6 dated Jun. 1, 2018, 4 pages.
Decision on Rejection in Chinese Patent Application No. 201280067035.6.
Examination Report in Great Britain Patent Application No. GB1408482.6.
Searrch and Examination Report in Great Britain Patent Application No. GB1408482.6.
Examination Report in Australian Patent Application No. 2017210662.
Exam Report No. 2 for AU App No. 2017210662 dated Jun. 21, 2018, 3 pages.
Search and Exam Report for GB App No. GB14084826 dated Mar. 28, 2018, 5 pages.
EP Office Action for application No. (12791665.8), dated Feb. 21, 2020, 4 pages.
Chinese Text of Notification of Reexamination Patent Application No. 2012800670356 dated May 5, 2019.
CN Office Action for CN App No. 201280067035.6 dated May 17, 2019, 5 pages.
EP Office Action for App No. 12791665.8 dated Mar. 26, 2020, 4 pages.
European Examination Report—Patent Application No. 12791665.8-1113 dated Sep. 17, 2019.

* cited by examiner

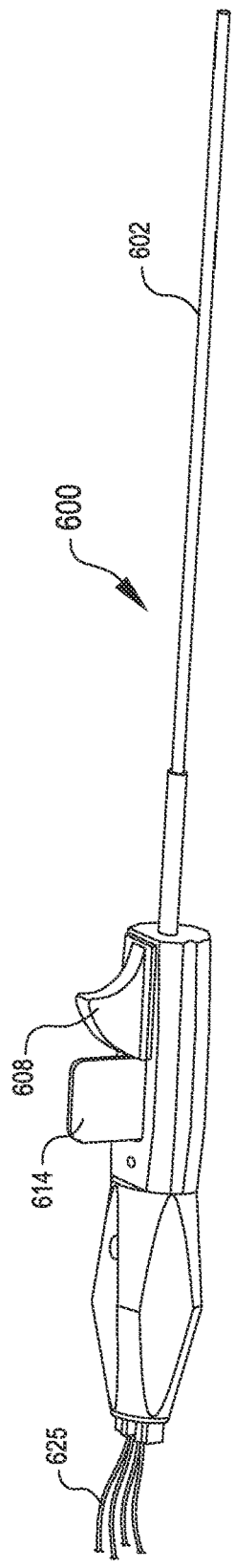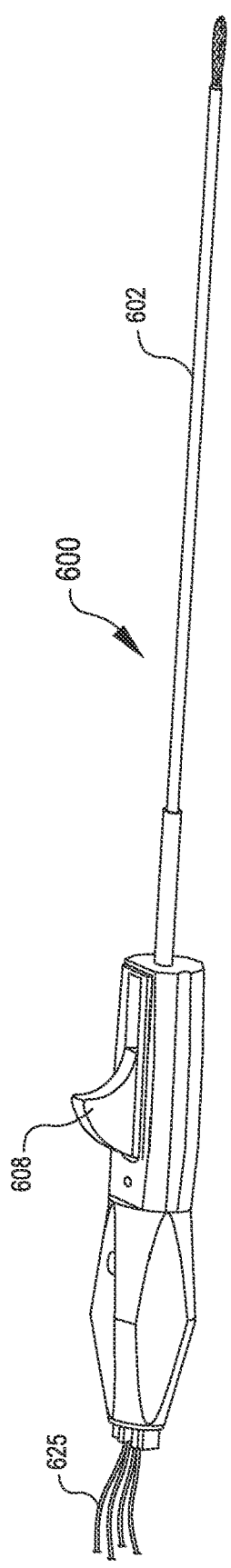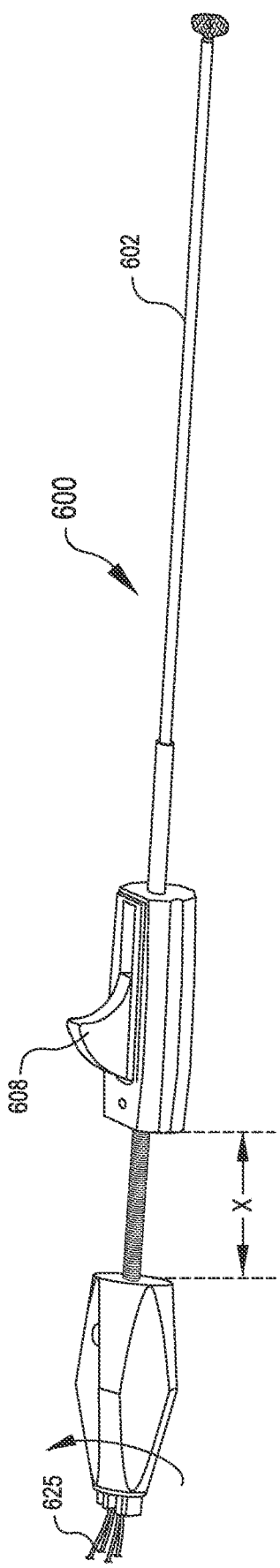

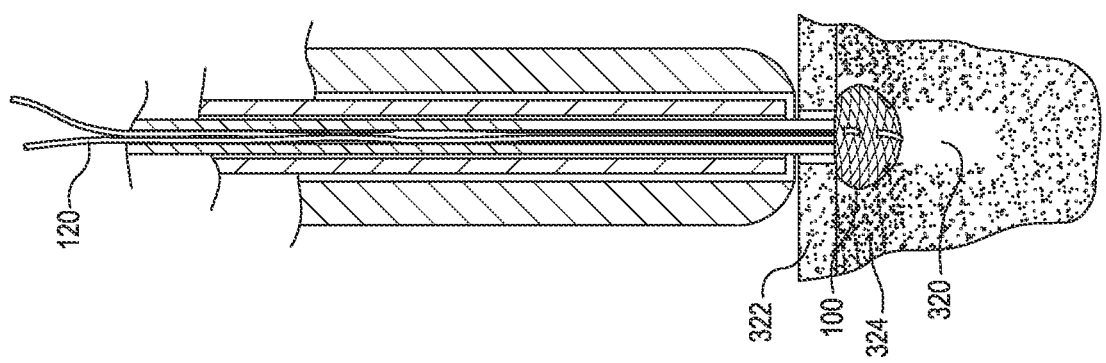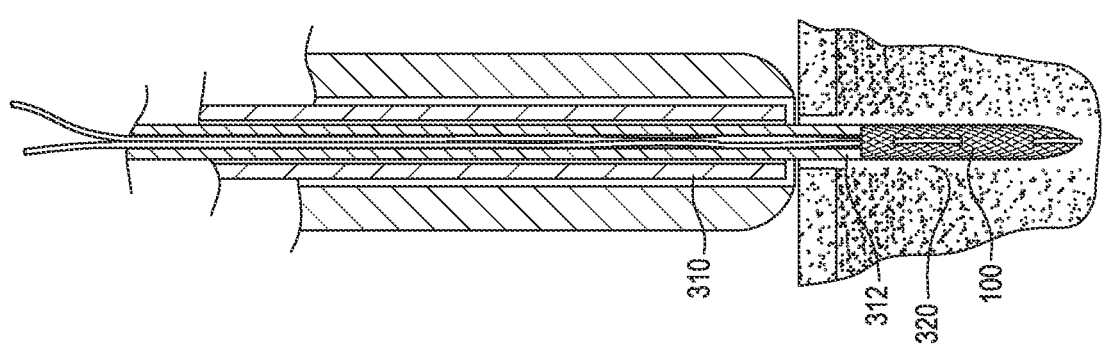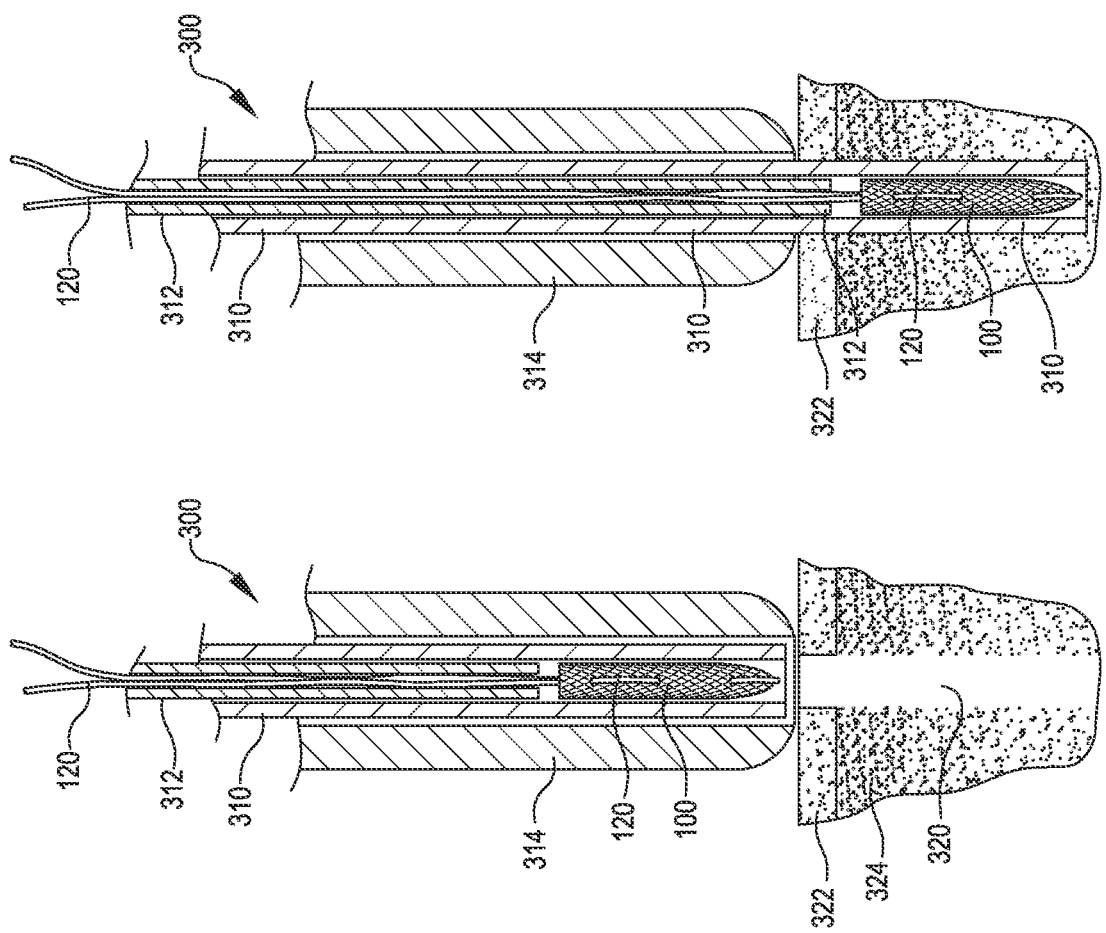

TISSUE REPAIR ASSEMBLY

CROSS-REFERENCE TO RELATED APPLICATIONS

This application is a continuation of U.S. application Ser. No. 13/677,112 filed Nov. 14, 2012, entitled "TISSUE REPAIR ASSEMBLY which claims priority to and benefit of U.S. Provisional Application No. 61/559,672, filed Nov. 14, 2011, the full disclosure of which is incorporated herein by reference.

BACKGROUND

There is an ever-increasing demand for more minimally invasive surgical techniques. The lower morbidity seen in endoscopic and arthroscopic surgery makes them very appealing to both patients and physicians. These technologically-advanced procedures include many forms of soft tissue to soft tissue repairs and soft tissue to bone repair. Examples of these (procedures in orthopedic surgery include rotator cuff repair, labral repair, biceps tenodesis, and anterior cruciate ligament reconstruction. Other examples in other surgical subspecialties include, but are not limited to, hernia repair, hysterectomies, and laparoscopic gastric bypass.

Many orthopedic surgery procedures involve the use of anchoring devices that attach soft tissue to bone. Most of these procedures and techniques rely on the use of polymers, metal, or biodegradable compounds. The use of these materials often requires relatively large holes placed in bone. If these devices ever loosen, one is faced with the issue of having a potentially hard device in a joint, which can place the patient at risk for developing arthritis. Certain polymeric devices, such as those made with polylactic acid (PLA), can weaken bone, predisposing the patient to fracture. Finally, metal devices can cause scatter on MRI, making follow-up MRI's inaccurate.

In addition, two major challenges facing all surgeons, and endoscopic surgeons in particular, are knot tying and suture management. Use of multiple sutures can lengthen procedure time, producing higher risk to the patient and lower repair predictability. Endoscopic knot tying is also very challenging. For example, arthroscopic soft tissue biceps tenodesis requires multiple passes of suture through the tendon and rotator cuff, followed by retrieval and knot tying which require a great deal of skill.

Solutions have been developed as an alternative to complex suture management, particularly for soft tissue to bone fixation. For example, a device that uses only soft, flexible materials in repairs has a number of key advantages: 1) The use of a less-invasive techniques for implantation because the use of a material that is less brittle allows the use of smaller holes in bone; 2) The ease of MRI use in follow-up; 3) No risk of a hard device lodging in a joint or body cavity; 4) Potentially better tissue incorporation, 5) Ultimately stronger bone and lower risk of fracture.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In embodiments, a tissue repair system is provided including a delivery mechanism and an anchoring implant which may be preloaded into the delivery mechanism. The anchoring implant may be configured to anchor within hard tissue such as bone or can act as a retaining anchor against softer tissue such as tendon or cartilage. One or more lengths of standard suture may be pre-attached to the anchoring implant.

In embodiments, the anchoring implants are generally soft and flexible in nature. For example, the anchoring implants can be constructed of suture combined with braided material created from suture material. This braided material may, in some embodiments, be constructed in a manner such that it creates a three-dimensional structure, such as that of a sock or an elongated five-sided box. Upon being deployed, the soft three-dimensional structure may expand, or be compelled to expand from a compressed state. Upon radial or horizontal expansion, the structure collapses to a shape that does not fit back through the hole through which it was introduced, thus anchoring or retention is achieved.

In further embodiments, one or more lengths of suture may be threaded into the above-referenced three-dimensional anchoring structure. The suture may be stitched into the braided material with a single or multiple stitches. If multiple stitches are used, those stitches can extend around an outer edge of the sock, starting at the opening, going to the toe, and returning up the other side to the opening, thus ultimately ending the stitching at the same end as its beginning. The suture may be tied or loose. If loose, the suture is slideable through the braided material of the structure. When the suture ends are tensioned with some counter traction against the braided material structure, the braided material structure compresses axially and expands radially.

In embodiments, the braided material of the anchoring implant is constructed from multiple woven or crocheted threads or fibers. These fibers may be woven in such a manner (e.g., braided) as to be in a substantially parallel orientation (with respect to the structure's axis) when the structure is in a relaxed or tensioned state. When the structure is in a compressed state, as when the sutures are tensioned with counter traction, the structure expands radially as the fibers are re-oriented into a substantially orthogonal orientation (in relation to the structure's axis).

In embodiments, the anchoring implant includes a braided pattern. More specifically, the structure utilized is a cylindrical, helically wound braid, such as the common biaxial braid. Pulling the entire braid along its length (i.e., putting the braid in tension) lengthens and narrows it. The length is gained by reducing the angle between the braided threads of the wound braid at the crossing points of the threads causing the braided threads to align mostly parallel, which also reduces the radial distance between opposing sides and hence the overall circumference. When counter traction occurs, the opposite action occurs, and the braid contracts axially and expands radially, in this case by increasing the angle between the braided threads.

In yet further embodiments of the anchoring implant, various methods of construction are shown to achieve a soft three-dimensional structure. These include but are not limited to use of a single flat section of braided material that is folded in half with the edges bound by various methods. Also presented is a tubular shaped braided material construct which may one end bound to create the sock configuration.

Other embodiments of the soft anchoring structure are disclosed, including one in which a strand of suture is coiled upon itself to form three-dimensional soft structure. Said coiled anchoring structure may be held together with the use of a binding substrate or with the use of stitches.

Another aspect of the invention involves various methods of using of a delivery tube to place and deploy the soft anchoring implant. In one approach, the implant may be loaded into the distal end of a delivery tube and deployed by using a pusher rod or tube to expel the implant. The implant would be deployed from the delivery tube in an axially aligned orientation from the proximal edge of a preformed hole in the tissue. An alternate embodiment involves placement of the preloaded delivery tube at the bottom of the preformed hole, then withdrawing or unsheathing the delivery tube and leaving the implant in the preformed hole.

Also disclosed herein are methods and apparatus for tensioning the soft suture anchor in place while counter traction is applied via a backstop mechanism. These methods and apparatus describe the tensioning of the sutures and implant to a predetermined distance and/or force such that more consistent and reliable retention is achieved.

Embodiments herein are directed to a method of anchoring tissue to bone, including boring a hole into bone of a human or an animal, inserting an inserter tube into the hole, the inserter tube having a soft anchoring implant mounted therein, a deployment rod mounted axially within the inserter tube and proximal of the soft anchoring implant, and a suture extending through the inserter tube and connected to a distal end of the soft anchoring implant with at least one end of the suture extending out of the hole; retracting the inserter tube while maintaining the soft anchoring implant in the hole and the deployment rod against the proximal end of the soft anchoring implant, the inserter tube being retracted at least to a proximal end of the soft anchoring implant; while maintaining the soft anchoring implant and a distal end of the deployment rod in the hole, pulling said at least one end of the suture to pull the distal end of the soft anchoring plant proximally, and shorten axially and expand radially the soft anchoring implant against the distal end of the deployment rod; and retracting the deployment rod from the hole while leaving the soft anchoring implant in the hole.

In embodiments, the soft anchoring implant includes a biaxial braid. The biaxial braid can include braided threads and when the soft anchoring implant is installed n the inserter tube, the angle between the braided threads of the wound braid is reduced at the crossing points of the braided threads causing the braided threads to align mostly parallel, which also reduces the radial distance between opposing sides and hence the overall circumference of the soft anchoring implant. Shortening the implant axially and expanding it radially can include increasing the angle between the braided threads.

In embodiments, the at least one free end of the suture can extend through the inserter tube. Pulling can include, as examples, at least one of tensioning the suture to a predetermined force or pulling the suture a predetermined distance to expand the anchor in the bone.

Embodiments are also directed to a method of anchoring tissue to bone, including boring a hole into bone of a human or an animal, the hole defining a longitudinal axis; inserting a soft anchoring implant into the hole with a deployment rod at the proximal end of the soft anchoring implant, the soft anchoring implant defining a tube aligned axially along the longitudinal axis, the tube defining distal and proximal ends and side walls, and the soft anchoring implant having a suture connected to a distal portion of the soft anchoring plant, with first and second ends of the suture extending from the proximal end of the soft anchoring implant; while maintaining the soft anchoring implant and a distal end of the deployment rod in the hole, pulling on the first and second ends of the suture to shorten axially and expand radially the soft anchoring implant against the distal end of the deployment rod; and retracting the deployment rod from the hole while leaving the soft anchoring implant in the hole. In embodiments, the tube is compressible and/or expandable.

The soft anchoring implant can be, for example, a biaxial braid. If so, in embodiments, the biaxial braid includes braided threads and, when the soft anchoring implant is installed in the inserter tube, the angle between the braided threads of the wound braid is reduced at the crossing points of the braided threads causing the braided threads to align mostly parallel, which also reduces the radial distance between opposing sides and hence the overall circumference of the soft anchoring implant. Shortening axially and expanding radially the biaxial braid includes increasing the angle between the braided threads.

In embodiments, pulling includes at least one of tensioning the suture to a predetermined force or pulling the suture a predetermined distance to expand the anchor in the bone.

In additional embodiments, an anchor for securing tissue to a bone or tissue to tissue is provided, the anchor including a soft anchoring implant comprising a biaxial braid and for inserting into a hole in bone or tissue of an animal or human, the soft anchoring implant comprising a tube aligned so as to define a longitudinal axis, the tube defining distal and proximal ends and side walls; and a suture connected to the soft anchoring implant, and extending parallel to the longitudinal axis along one side of the sidewalk, across the distal end, and returning parallel to the longitudinal axis along an opposite side of the sidewalls, with first and second ends of the suture exiting adjacent the proximal end of the implant; wherein tensioning the first and second ends of the suture when the soft anchoring implant is installed in a hole in bone or through the tissue of an animal or a human causes the implant to change from a first configuration where the tube of soft anchoring implant is elongate into a second configuration where the tube is compressed axially and extended radially so as to form an anchor in the hole. The biaxial braid can include braided threads and, when the soft anchoring implant is installed in the inserter tube, the angle between the braided threads of the wound braid is reduced at the crossing points of the braided threads causing the braided threads to align mostly parallel, which also reduces the radial distance between opposing sides and hence the overall circumference of the soft anchoring implant. Shortening axially and expanding radially can be done, for example, by increasing the angle between the braided threads.

In still further embodiments, a method of anchoring tissue to bone is provided, including boring a hole into bone of a human or an animal, the hole defining a longitudinal axis; inserting a soft anchoring implant into the hole with a deployment rod at the proximal end of the soft anchoring implant, the soft anchoring implant comprising a structure aligned axially along the longitudinal axis, the structure defining distal and proximal ends and side walls, and the soft anchoring implant being inserted in the hole in a retracted configuration where the side walls are retracted such that a diameter of the soft anchoring implant is smaller in diameter than a diameter of the soft anchoring implant when the soft anchoring implant is in a relaxed state; expanding the soft anchoring implant to a diameter larger than its relaxed state against the distal end of the deployment rod; and retracting the deployment rod from the hole while leaving the soft anchoring implant in the hole. Inserting can include inserting the soft anchoring implant from an inserter tube into which the soft anchoring implant is mounted, the inserter tube confining the soft anchoring implant into the retracted configuration. Inserting can also or alternatively include inserting the inserter tube into the hole with the implant therein.

In still further embodiments, a method of deploying a soft suture anchor implant is provided, including drilling a hole in the bone of an animal or human; inserting a soft anchoring implant into the hole, the soft anchoring implant having a suture connected thereto; and tensioning the suture to a predetermined force to expand the soft anchoring implant in the bone. Tensioning can be accomplished, for example, by twisting a knob in the inserter handle or by activating a lever on the inserter handle.

In yet still more embodiments, a method of deploying a soft suture anchor implant is provided, including drilling a hole in the bone of an animal or human; inserting a soft anchoring implant into the hole, the soft anchoring implant having a suture connected thereto; and pulling the suture a predetermined distance to expand the soft anchoring implant in the bone. Pulling the suture a predetermined distance can be accomplished, for example, by twisting a knob in the inserter handle or by activating a lever on the inserter handle.

In additional embodiments, an anchoring implant for anchoring a suture to bone or tissue is provided, including an implant constructed of a biaxial braided material and a suture connected to the implant. The biaxial braided material can be configured to define a resident volume when in a relaxed state, a substantially reduced resident volume when loaded into an insertion device, and substantially no resident volume when fully deployed to tissue.

In embodiments, a device for installing a suture anchor into a human or animal patient is provided, including a handle; an inserter tube connected to the handle, the inserter tube defining a longitudinal axis and an elongate pocket inside the insert tube, arranged along the longitudinal axis, and for receiving an implant; a deployment rod slidably received in the inserter tube and proximal of the pocket; the inserter tube, the deployment rod, and the handle defining an internal passageway for a suture that attaches to an implant in the pocket; and an actuator for translating the deployment rod relative to the inserter tube which, when an implant is in the pocket, and the actuator is actuated, the deployment pushes the implant out of the pocket. A suture puller mechanism can be included for tensioning a suture that extends through the passageway and is attached to an implant, the suture puller being configured to pull the suture after the deployment rod has pushed the implant out of the pocket, so that the suture tensions the implant against a distal end of the deployment rod. The suture puller mechanism can include a mechanism for limiting pulling of the suture to a predetermined distance and/or a mechanism for limiting pulling of the suture to a predetermined force.

Additional embodiments are directed to a method of anchoring tissue to tissue, including passing an inserter tube through one or more pieces of tissue such that an open end of the inserter tube extends beyond the tissue, the inserter tube containing one or more soft anchoring implants, each of said soft anchoring implants defining a tube aligned axially along the longitudinal axis, the tube defining distal and proximal ends and side walls, and the soft anchoring implant having a suture connected to a distal portion of the soft anchoring plant, with first and second ends of the suture extending from the proximal end of the soft anchoring implant; for each of said plurality of soft anchoring implants: pushing the soft anchoring implant into the space on the opposite side of the tissue, retracting the insertion tube while leaving the soft anchoring implant on the other side of the tissue, and pulling on the suture to shorten axially and expand radially the soft anchoring implant against the tissue surface to provide retention.

For a more comprehensive understanding of the nature and advantages of the present invention, reference should be made to the ensuing detailed description and accompanying drawings.

BRIEF DESCRIPTION OF THE DRAWINGS

FIG. 21A is a perspective view of the tissue repair delivery system with implant loaded.

FIG. 21B is a perspective view of the tissue repair delivery system with implant deployed.

FIG. 21C is a perspective view of the tissue repair delivery system with implant deployed and tensioned/expanded.

FIG. 28 is a section view showing the tissue repair system of FIG. 27 preloaded into the delivery system and place over a preformed hole in the tissue.

FIG. 29 is a section view showing the soft anchoring implant of FIG. 28 still housed within the inserter tube of the tissue repair delivery system after the inserter tube has been pushed to the bottom of the preformed hole in the tissue.

FIG. 30 is a section view showing of the tissue repair delivery system of FIG. 29 after the inserter tube has been retracted to expose the soft anchoring implant.

FIG. 31 is a section view showing the tissue repair delivery system of FIG. 30 after the soft anchoring implant has been deployed into its anchoring state.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The technology disclosed herein would have a broad application in orthopedic surgery for an animal, such as a human. This includes repairs of tendons to bone, bone to bone, tendons to tendons, and ligaments to bone, including ligament reconstruction. Some of these procedures include, but are not limited to, labral repairs in the shoulder and hip, capsular plication, biceps tenodesis, anterior cruciate ligament reconstructions, rotator cuff repairs, meniscal repair, triangular fibrocartilage (TFCC) repairs, and ankle stabilization. There can also be an application for fracture repair, such as for repairing small butterfly fragments in long bone fractures.

Applications outside of orthopedic surgery include: cardiac surgery (where pledgets are used in the implantation of prosthetic heart valves), general surgery (for hernia repair, nissen fundoplication, and parenchymal compression), plastic surgery (for tissue to tissue repair), Ob-Gyn (for cuff closure in laparoscopic hysterectomy and bladder support).

Figure 1:
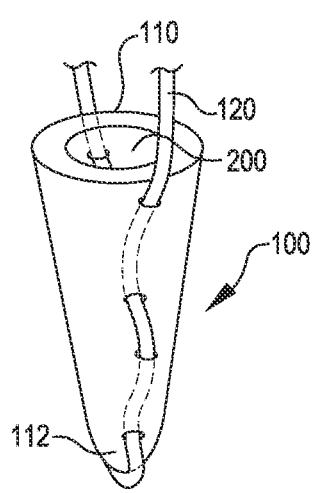
FIG. 1 is a perspective view of a soft anchoring implant shown with a single suture threaded through it.

Referring now to the drawings, in which like reference numerals represent like parts throughout the several views, FIG. 1 is a perspective view of a soft anchoring implant 100 with an associated length of suture 120 passed through it. When used as part of the tissue repair system, the implant 100 is intended to anchor suture within bone or other hard tissue and allow for the further attachment of soft tissue as in an orthopedic repair. In embodiments, the soft anchoring implant 100 may be loaded into a delivery system and deployed into hard tissue such as bone to facilitate a repair or deployed as a retaining anchor for two pieces of soft tissue. In other embodiments, the tissue repair system may be utilized as described herein to facilitate the attachment of synthetic tissue or materials to other structures within the body.

Generally described, the soft anchoring implant 100, is three-dimensional, tubular shape with one open end 110 and one closed end 112 and defining a resident volume 200 (discussed in detail later). The implant would typically be sized in the range of 10 mm-30 mm in length with a width or diameter of 2 mm-6 mm. A length of suture 120 of the type typically used in orthopedic repair procedures is shown passed outside and around the proximal end of the soft anchoring implant 100 in FIG. 1 and subsequent figures. The suture 120 passes through the wall of the implant to the outside for a short distance before it passes back to the inside of the implant, then out again and around the closed end of the implant before repeating the penetrations and exiting back out around the open, proximal end of the implant 100. The suture length 120 is not locked into place with respect to the soft anchoring implant 100, rather it remains slideable through or along the walls of the implant. This slideability aspect is important to the function of the implant as it relates to its ability to attach and repair tissues.

A second function of the suture length 120 is in the deployment aspect utilizing the tissue repair system. When the suture lengths are tensioned and some counter traction is applied at the end 110 of the anchoring implant 100, the anchoring implant shortens along its axis and in doing so expands radially. This radial expansion forces the anchoring implant to assume a larger effective diameter than it had prior to deployment and larger than the hole into which it was inserted. Thus the anchoring aspect is achieved.

Figure 2:
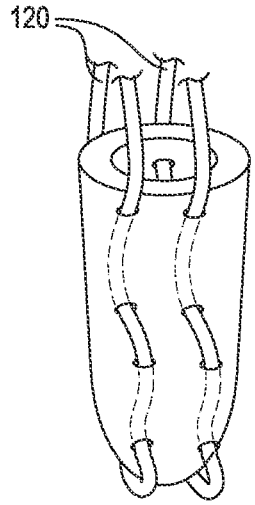
FIG. 2 is a perspective view of the soft anchoring implant shown with multiple sutures threaded through it.
Figure 3:
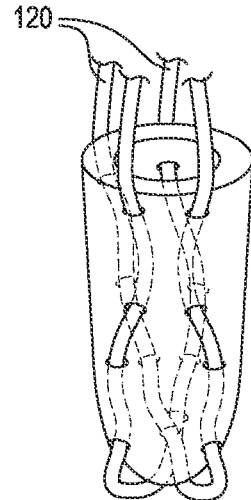
FIG. 3 is a perspective view of the soil anchoring implant shown with two sutures threaded through it in a crossing configuration.

FIG. 2 shows an alternate embodiment of the soft anchoring implant with two suture lengths 120 passed through it in a side-by-side fashion. Alternatively, FIG. 3 shows the soft anchoring implant with two suture lengths 120 passed through it in a cross-over fashion. Having multiple suture lengths may have the added benefit in the surgical procedure of being able to anchor multiple pieces of tissue independently to the bone or other tissue where the soft anchoring implant resides. Multiple sutures also allows for the use of a greater variety of suturing and repair techniques. Additionally, multiple suture strands may allow for more effective deployment of the soft anchoring implant into the bone or other hard tissue by virtue of the fact that they may inherently cause more wrinkling, folding, or puckering of the soft anchoring implant thus giving it better retention properties, In additional embodiments, the soft anchoring implant can include three or more suture lengths associated with it. It is understood that these suture lengths may be configured in a sided-by-side fashion or in any variety of cross-over fashion. It is also understood that the suture lengths may initiate interface with the soft anchoring implant through an inside of the lumen or from the outside the lumen and may enter and exit the walls of the soft anchoring implant once or multiple times.

Figure 4:
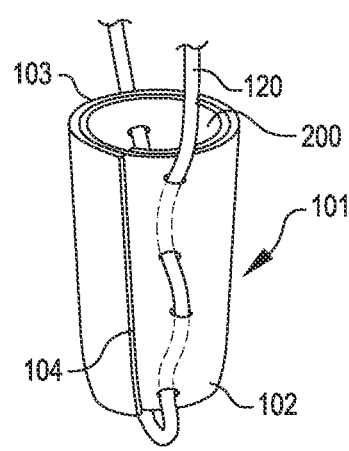
FIG. 4 is a perspective view of the soft anchoring implant constructed from braided material that is rolled into a conical shape.
Figure 5:
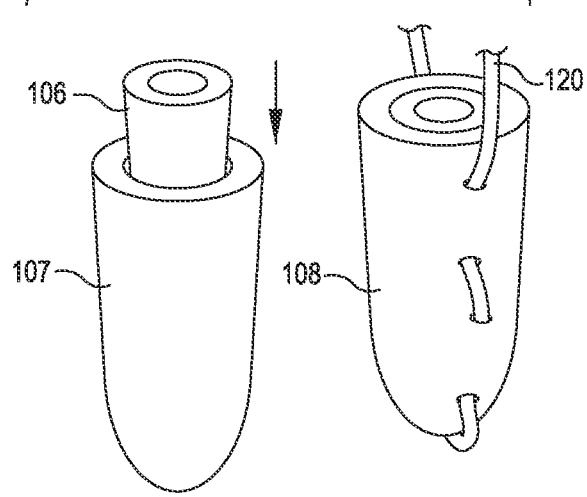
FIG. 5 is a perspective view of the soft anchoring implant constructed by layering two braided material structures.

FIG. 4 shows an embodiment of a soft anchoring implant 101 constructed from a flat section of braided material that has been rolled into a tube or cone shape. The rolled structure 101 may be held together with adhesive or stitches and the free edge 104 of the braided material may be bound further in similar methods. This rolling of the braided material may provide added thickness to the structure for the purposes of enhanced retention properties. Similar to other embodiments, the braided material may be rolled upon itself in such a manner as to partially or completely close one end while leaving the opposite end 103 substantially more open and creating a resident volume 200. Alternatively, it may be rolled into a straight tubular configuration with both ends equally open or closed. As with other embodiments, a length of suture 120 may be stitched through the braided material to facilitate the deployment of the soft anchoring implant, FIG. 5 is another embodiment of a soft anchoring implant showing an alternative layering construction. In this embodiment one braided material structure 106 is nested inside another braided material structure 107 to create a double-layered structure 108. This construction method may be multiplied as desired, to create triple-layer structures and more. This layering configuration creates a structure with thicker walls which may be advantageous for applications requiring higher retention strength. This added thickness may also allow the use of a smaller gage suture strand(s) as the strand will be less likely to destructively pull through braided structure.

Figure 6:
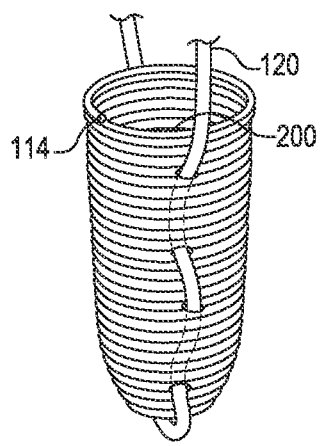
FIG. 6 is a perspective view of another embodiment of a soft anchoring implant shown as constructed from a single suture coiled upon itself in a stacking manner.

FIG. 6 shows yet another embodiment of the soft anchoring implant that is formed from single or multiple continuous strands 114 of suture that are coiled upon themselves to form a tubular construct that may contain a resident volume 200. In this embodiment, the strand(s) 114 are coiled upon itself in a stacking fashion with the resulting geometry similar to that of previous embodiments and defining a resident volume 200. The layers of coiled suture may be held together by a substrate such as an adhesive that allows it to remain soft and flexible. Alternatively the stacks may be bound together by tacking sutures. A suture length 120 may be passed through braided material in a similar manner as prior embodiments. The coiled suture structure may be a straight tubular configuration with a consistent diameter or alternatively could be conical shaped, so as to have a very small diameter (even closed) on one end with a much larger diameter on the other end.

Figure 7:
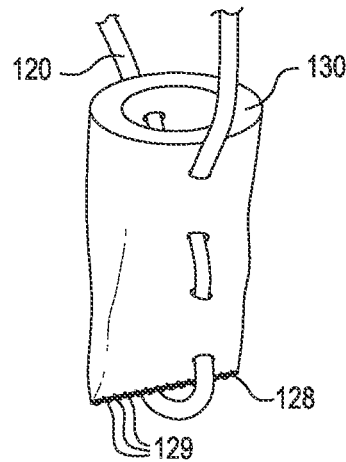
FIG. 7 is a perspective view of another embodiment of a soft anchoring implant shown as constructed from braided material in a tubular shape with a distal end bound shut.

FIG. 7 shows an alternate embodiment of the soft anchoring implant in which a distal end 128 is bound closed with stitching 129. Again, the suture length 120 is passed through the soft anchoring implant, encompassing the closed end, with both free ends of suture 120 exiting the implant outside and around the open end 130. It is understood that the bound end 128 may be closed by heat sealing or any other reasonable method of closing the end.

Figure 8:
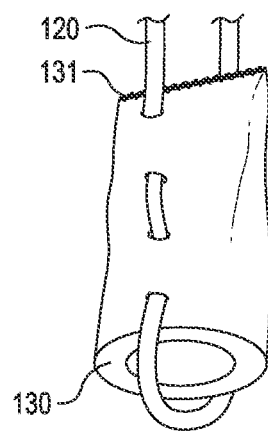
FIG. 8 is a perspective view of another embodiment of a soft anchoring implant shown as constructed from braided material in a tubular shape with a proximal end bound shut, the suture strand originating from the shut end.

FIG. 8 shows an alternate embodiment of a soft anchoring implant in which one end 131 is bound closed by heat sealing. The suture length 120 is passed through the soft anchoring implant, starting at the bound end, going down the side wall of the implant and encompassing the open end 130, with both free ends of suture 120 exiting the implant at the bound end 131. It is understood that the bound end 131 may be closed by stitching or any other method of closing the end of the implant.

Figure 9:
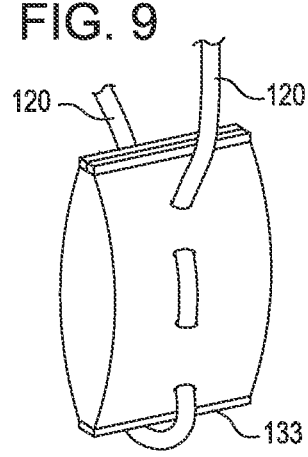
FIG. 9 is a perspective view of another embodiment of a soft anchoring implant shown as constructed from a braided material in a tubular shape with one both ends bound shut.

FIG. 9 shows an alternate embodiment of a soft anchoring implant in which both ends 133 are bound closed by heat sealing or stitching. As with other embodiments, the suture strand runs down one side of the implant, around the opposite bound end and up the other side, with both ends of suture exiting the same end. As with other embodiments, the suture may penetrate the walls of the implant one or more times. This embodiment may contain a resident volume that is completely enclosed.

Figure 10:
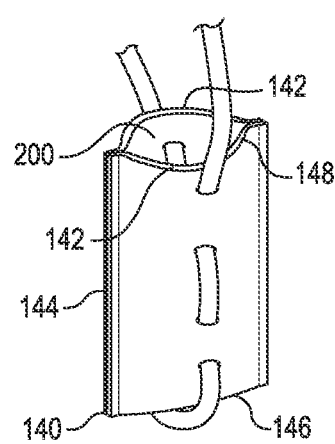
FIG. 10 is a perspective view of still another embodiment of a soft anchoring implant shown as constructed from a flat section braided material folded in half with the sides bound shut with adhesive.

FIGS. 10 through 13 are perspective views of alternate embodiments of soft anchoring implants with sutures. These figures represent various methods of constructing a three-dimensional tubular implant from a flat piece of suture-based braided material. In FIG. 10, a flat rectangular length of suture braided material has been folded in half such that the folded portion 140 creates the closed end 146 of the soft anchoring implant and the two free ends 142 are aligned to form the open end 148. The sides of the rectangular braided material where the edges 144 meet are bound closed with adhesive. It is important to note the two halves of folded braided material are not bound all the way across, rather only at the edges so as to create an open space or resident volume 200 at the center of the three-dimensional soft anchoring implant. The resident volume will be further discussed and defined later. As in previous embodiments, a suture length 120 may be threaded in-and-out of the soft anchoring implant that encompasses the closed end 146, with both free suture ends exiting around the open end 148.

Figure 11:
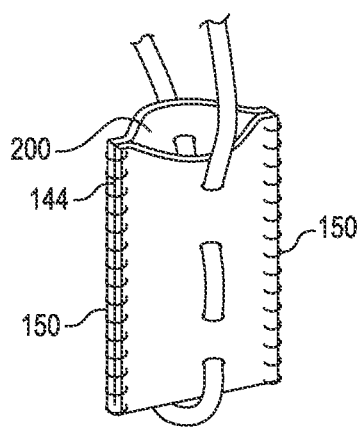
FIG. 11 is a perspective view of yet still another embodiment of a soft anchoring implant shown as constructed from a flat section braided material folded in half with the sides bound shut by sewing.
Figure 12:
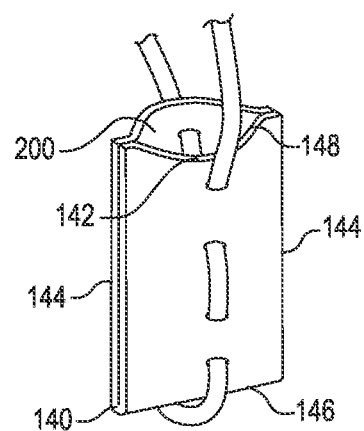
FIG. 12 is a perspective view of another embodiment of a soft anchoring implant shown as constructed from a flat section braided material folded in half with the sides bound shut by heat sealing.

FIG. 11 shows a soft anchoring implant similar that of FIG. 10 which has been formed from a rectangular piece of suture-based braided material that has been folded in half upon itself. All aspects remain the same except that in this embodiment, the two side edges of the braided material 144 have been bound closed by a running or interrupted stitch 150 that runs the length of the implant. Again, only the edges are bound so as to create the resident volume, FIG. 12 shows a soft anchoring implant similar that of FIGS. 10 and 11 which has been formed from a rectangular piece of suture-based braided material or braided material that has been folded in half upon itself. All aspects remain the same except that in this embodiment, the two side edges of the braided material have been heat-sealed closed as is a common manufacturing technique with polymer-based braided materials and suture. As before, the soft anchoring implant retains a three-dimensional configuration and may have a resident volume 200.

Figure 13:
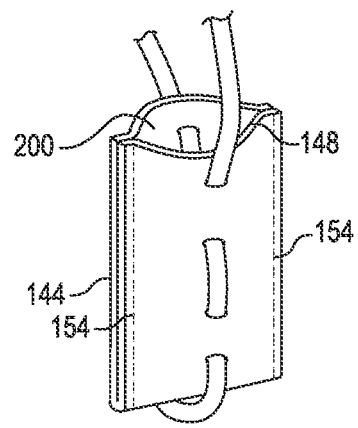
FIG. 13 is a perspective view of even another embodiment of a soft anchoring implant shown as constructed from a flat section braided material folded in half with the sides bound shut by mattress stitching.

FIG. 13 shows a soft anchoring implant similar that of FIGS. 10-12 and which has been formed from a rectangular piece of suture-based braided material or braided material that has been folded in half upon itself. All aspects remain the same except that in this embodiment, the two side edges of the braided material have been closed using a mattress-type stitch 154 that effectively binds the edges together without the stitch loop actually encompassing the open edges 144 themselves. As before, the soft anchoring implant retains a three-dimensional configuration with a resident volume 200.

While it is stated that the soft anchoring implants shown in FIGS. 9 through 13 may be constructed from a piece of rectangular-shaped braided material that is folded in half, it should be clear that the rectangular shaped braided material could be any elongated braided material shape including two separated pieces of elongated braided material that are attached to one another to create a three-dimensional construct with a resident volume 200 as shown in the figures.

In the figures, the soft anchoring implant is in the form of a three dimensional structure like that of a sock or a closed end tube or a five-sided box. This three-dimensional structure preferably defines or includes a predefined inner space or resident volume 200. The "resident volume" is a volume that is intentionally formed by the three-dimensional anchoring implant structure in its manufactured, predeployed or relaxed state. A resident volume as defined herein may be inherently thicker and/or wider than the thickness of the material from which the structure is fabricated. For example, a flat piece of braided material with a hole in it may not define a resident volume (the hole), because the hole is only as deep as the thickness of the braided material. It is not necessarily a permanently open or enclosed volume. For example, as in the case of soft flexible braided materials, said resident volume may exist upon manufacture and inherently in the structure, but when the sides of the structure are compressed, the resident volume may become smaller or disappear altogether. The resident volume may exist as manufactured in the structure of the anchoring implant when the implant resides in an upright configuration but tend to disappear when the structure is on its side due to the forces of gravity on the soft, flexible braided material of the structure. However, the resident volume always exists within the structure when the structure is returned to its original position and configuration. The term as it is used herein does not necessarily preclude the resident volume from being filled with some other substance at a given time nor does it preclude the structure folding or collapsing in on itself so as to temporarily Obscure the presence of the resident volume.

The soft anchoring implant as shown in FIGS. 1-13, is preferably a soft, flexible construct of braided yarns or fibers. It may be of benefit for this construct to be constructed from known biocompatible materials commonly used in orthopedic procedures such a suture. Typical materials that would be used to construct the implant may be but are not restricted to Ultra high molecular weight polyethylene (UHMP), Polyester, Polyproylene, Silk or bioabsorbable materials typically used for suturing applications. The suture length 120 that is passed through the soft anchoring implant 100 is of a gage and material typically used in orthopedic surgical procedures. For example, a #2 size suture length would typically be used for the suture length 120 in a construct designed for rotator cuff repair or labrum repair in the shoulder. A #1 suture can also be used with the smaller implants.

Figure 14:
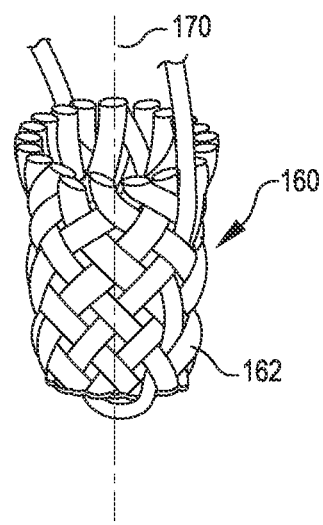
FIG. 14 is a side view of a soft anchoring implant formed of coarse, braided material, with the braided material in a relaxed, as-manufactured state prior to deployment showing the vertical orientation of the fibers.

As mentioned earlier, the soft anchoring implant may be constructed of a soft, flexible construct of braided yarns or fibers. The orientation of the fibers within the construct as well as the actual fiber diameter and the tick size of a braided material are of some importance in the expansion of the soft anchoring implant during deployment. FIG. 14 shows an embodiment of the soft anchoring implant in the pre-deployed state 160 in which the fibers are relaxed in an orientation neither substantially parallel with the axis 170 nor orthogonal to the axis 170 of the construct. In this state the soft anchoring implant may assume a width or diameter of "D" which is typically in the range of 0.1" to 0.25" and a length of "L" which is typically in the range of 0.45" to 0.9". The loose fiber or yarns at the open end may be bound to one another with heat sealing or other methods so as to prevent fraying.

Figure 15:
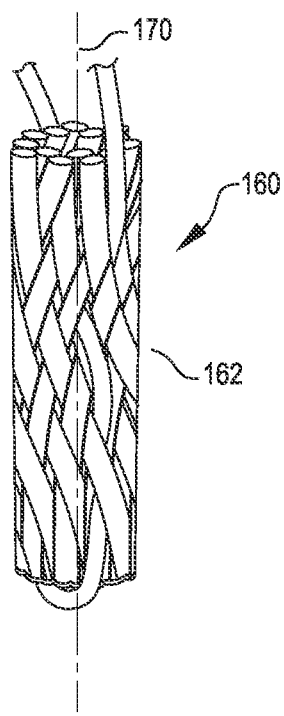
FIG. 15 is a perspective view of the soft anchoring implant of FIG. 14 in an elongated, compressed state prior being loaded into the inserter.

The soft anchoring implant my then be placed into an en elongated and compressed state as shown in FIG. 15. The fibers of the implant are more aligned in an orientation parallel to the axis 170 and are generally more compacted. In this orientation, the soft anchoring implant is generally in a more elongated state and of a generally smaller diameter with a typical width or diameter "D2" of 0.06" to 0.150" and length "L2" of 0.5" to 1.0". This implant may be pulled and manually manipulated to achieve this configuration or the use of specialized manufacturing fixtures may be employed, such as a funnel or a tube, which may compel the implant to achieve this configuration to better fit within the inserter tube.

The embodiment shown in FIG. 15 is formed from a coarse braided material. More specifically, the structure utilized is a cylindrical, helically wound braid, such as the common biaxial braid. Pulling the entire braid along its length (i.e., putting the braid in tension) lengthens and narrows it. The length is gained by reducing the angle between the braided threads of the wound braid at the crossing points of the threads so that the braided threads align mostly parallel, which also reduces the radial distance between opposing sides and hence the overall circumference. When counter traction occurs, the opposite action occurs, and the braid contracts axially and expands radially, in this case by increasing the angle between the braided threads. This helically wound braid provides an advantage in that the structure can collapse and elongate naturally due to the alignment of the braids.

Figure 16:
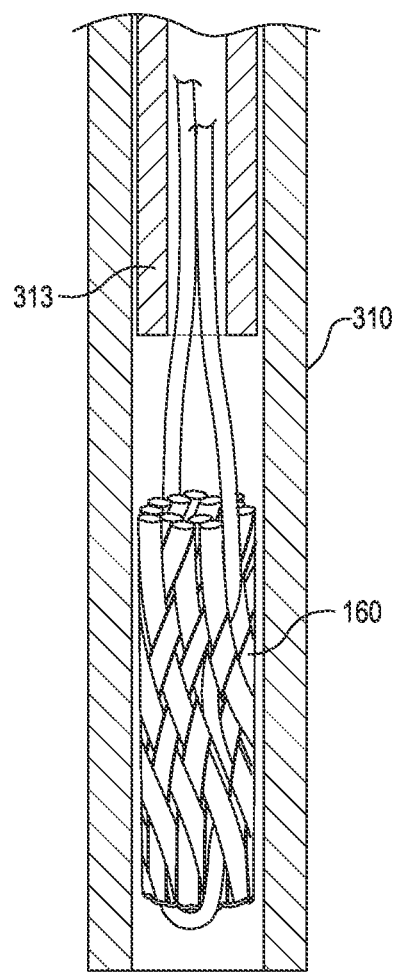
FIG. 16 is a partial section view of the soft anchoring implant of FIG. 15 in an elongated, compressed state loaded in the inserter tube.
Figure 17:
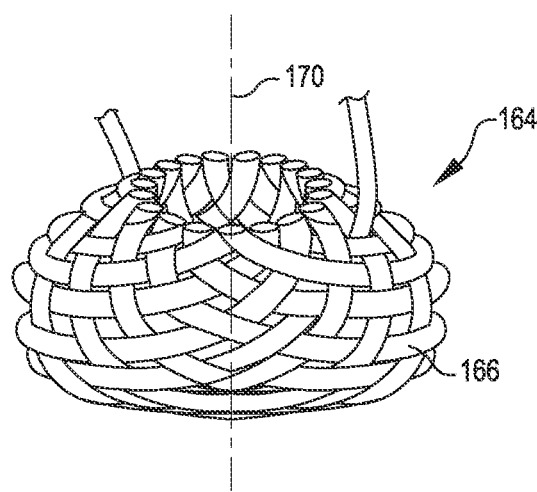
FIG. 17 is a side view of the soft anchoring implant of FIG. 14 in a compressed state after deployment showing the substantially horizontal orientation of the fibers.

FIG. 16 shows the implant of FIG. 14 in its elongated, compressed state and loaded into an inserter tube 310 in preparation for insertion in tissue and eventual deployment. The easily collapsible structure of the helically wound braid permits an installer to quickly and efficiently stretch the implant to the elongate position, and insert it into the inserter tube 310. Upon deployment of the soft anchoring implant by tensioning the sutures as described earlier, the fibers of the textile assume an orientation more orthogonally aligned 166 with respect to the axis 170. FIG. 17 shows this post-deployed state 164, wherein the implant is generally shortened and of a larger diameter than in the pre-deployed state 160. As described previously, the inherent fiber size in textile or braided material combined with the weave or opening or tick size may impact the ability of the implant to achieve varying degrees of the predeployed and postdeployed states.

A fiber or yarn size of 200 to 1500 denier is generally appropriate with a braid of 7 to 25 pies per inch (PPI). Tightly braided constructs made of small fibers, for example 100 denier at 50 PPI would not allow the orientation change of the fibers which facilitate the contraction and expansion of the implant and thus inherently have lower retention strength. Woven constructs are similarly restricted in their expansion capability due the orientation of the fiber weave.

The ratio of the implant length to diameter (or width) of the soft anchoring implant may play some role in achieving better retention properties. For example, a longer implant of a given diameter may better anchor itself in tissue by virtue of the fact that it would have more surface area contact with the surrounding tissue or bone. Alternatively, there may be some benefit to a soft anchoring implant with a relatively large diameter (or width) in relation to the hole through which it is pushed. There are limitations to the diameter of the implant however, as imposed by the space within inserter tube used to deploy the implant. However, in embodiments, a soft anchoring implant may fit into an inserter tube or other delivery mechanism with a smaller diameter. This is possible because of the soft, flexible nature of the implant, with its combination of yarn size and pie count allowing it to elongate and compress to a substantially smaller diameter to allow for placement into an inserter tube without necessarily folding over on itself.

Figure 18:
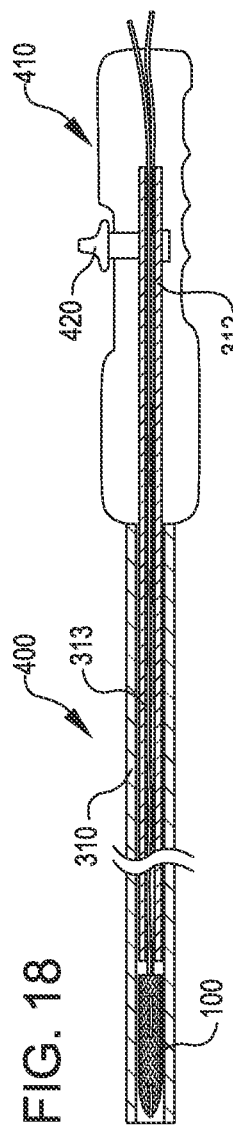
FIG. 18 is a section view of an embodiment of a tissue repair delivery system.

FIG. 18 is a section view of a deployment system 400 of the tissue repair assembly. A hand piece 410 is shown with the inserter tube 310 attached at the distal end. A slider 420 is operatively attached to an implant pusher 312 and moves it back and forth relative to the inserter tube 310. The implant pusher 312 can be a rod or a tube, and if a tube, suture can be routed up the tube from the implant to a handle for the hand piece 410. The distal end 313 of the implant pusher 312 is coaxially disposed within the inserter tube 310. In an alternate embodiment the implant pusher 312 may remain stationary with respect to the handle 410, while the inserter tube 310 is moveable. The soft anchoring implant 100 is shown disposed in the end of the inserter tube 310 and resting just distal to the end of the implant pusher 312.

Figure 19:
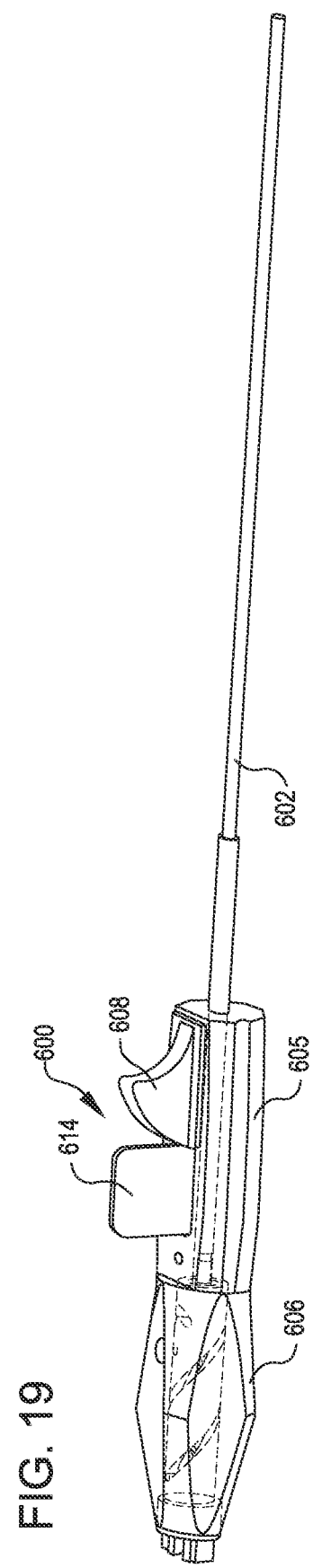
FIG. 19 is a perspective view of the tissue repair delivery system of FIG. 18.

FIG. 19 is another embodiment of a delivery system. The hand piece 600 is primarily comprised of a handle body 605 and a knob shell 606, with a slideable trigger 608 moveable within the handle body. Attached to the trigger 608 is the inserter tube 602, such that retracting the trigger 608 also retracts the inserter tube 602 relative to the implant pusher 601 which is disposed coaxially within the inserter tube 602. The implant pusher 601 is immovably anchored to the handle body 604 via a set screw or other mechanical attachment or bonding means.

Disposed coaxially within and immovably attached to (via screws, adhesives or other mechanical fasteners) the knob shell 606 is a helix bushing 610 (FIG. 20) which has a helical groove cut through the wall. A helix pin 620 which protrudes from a post of the handle body 604 slides within the groove on the helix bushing 610. Thus by twisting the knob shell 606 with attached helix bushing 610, the helix pin 620 slides down the groove in the helix pin 610 and moves the knob shell 606 with helix bushing distally by the length of the groove.

It is understood that this helix bushing with groove is a means of translating the twisting motion into a linear motion and this may be achieved using a thread-type mechanism as well.

At the proximal end of the knob shell 606 is the suture retention disc 612 which has a hole through which the suture tails are threaded (not shown) and at least one suture post 613 onto which the suture tails are removably attached when implant is loaded.

Turning back to the hand piece 600 in FIG. 19, a safety tab 614 sits behind the trigger 608 preventing it from being retracted. Once the safety tab 614 is removed, the trigger 608 may be retracted and thus retracting the inserter tube 602 relative to the backstop and exposing the implant (not shown).

Figure 20:
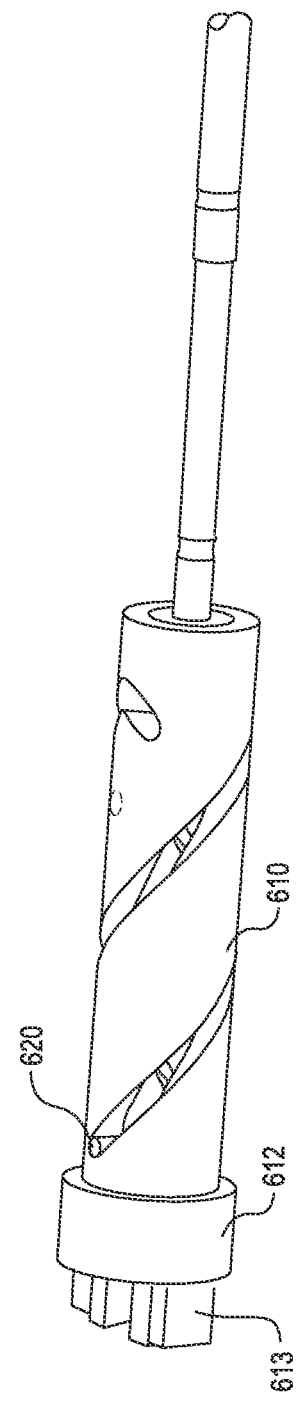
FIG. 20 is a perspective view of internal components of the tissue repair delivery system of FIG. 19.

FIG. 21A shows the delivery system of FIGS. 19-20 with an implant (not visible) preloaded into the distal end of the inserter tube 602 and suture tails 625 extending from the proximal end of the hand piece 600, The safety tab 614 is in place behind the trigger 608, indicating that no deployment has taken place.

FIG. 21B shows the preloaded delivery system of FIG. 21A. In this view the safety tab 614 has been moved out of the way, and the trigger 608 has been retracted, thus retracting the inserter tube 602 and exposing the soft anchoring implant 627. At this stage, the soft anchoring implant 627 is in its compressed, elongated state. In this state the implant 627 is at a diameter roughly equivalent to the inner diameter of the insertion tube. There may be some inherent slight expansion in diameter of the implant as the inserter tube 602 is retracted from around it, thus allowing it t any empty space left by the inserter tube.

FIG. 21C shows the delivery system of FIG. 21B with the knob shell 606 shown in a retracted position. This was accomplished by twisting the knob shell 606 such that the helix or screw thread) mechanism described earlier effects a linear translation along the post 629 of the handle body 604. By translating the knob shell 606 by the distance X, tension is applied to the sutures 625 which are anchored to the suture retention disc 612 via the suture post 613. This tension applied to the sutures compresses the soft anchoring implant 627 and effects a change in orientation of the axially-aligned fibers or yarns to an orientation more orthogonal to the axis, thus enlarging the effective diameter of the implant 627. The distance X is typically in the range of 0.75" to 2" and inherently creates a tensile force Y on the sutures which in turn creates an equal compressive force on the implant. This tensile force Y is typically directly related to the travel distance X but also dependent upon the resistance of the tissue, stiffness of the sutures, etc. This tensile force Y is ideally in the range of 50N to 200N force in order to adequately tension the sutures to create good retention of the implant, particularly in bony tissue. An optimal configuration may tension the sutures a distance of approximately 1.6", corresponding to a tensile force in some tissue formations of about 140N. Alternatively, an inserter can be configured to apply a given force, regardless of distance travelled. For such embodiments, force could release due to a friction hold on the sutures, a breakaway tab, a measurement device, or another structure or force measurement device.

Figure 22:
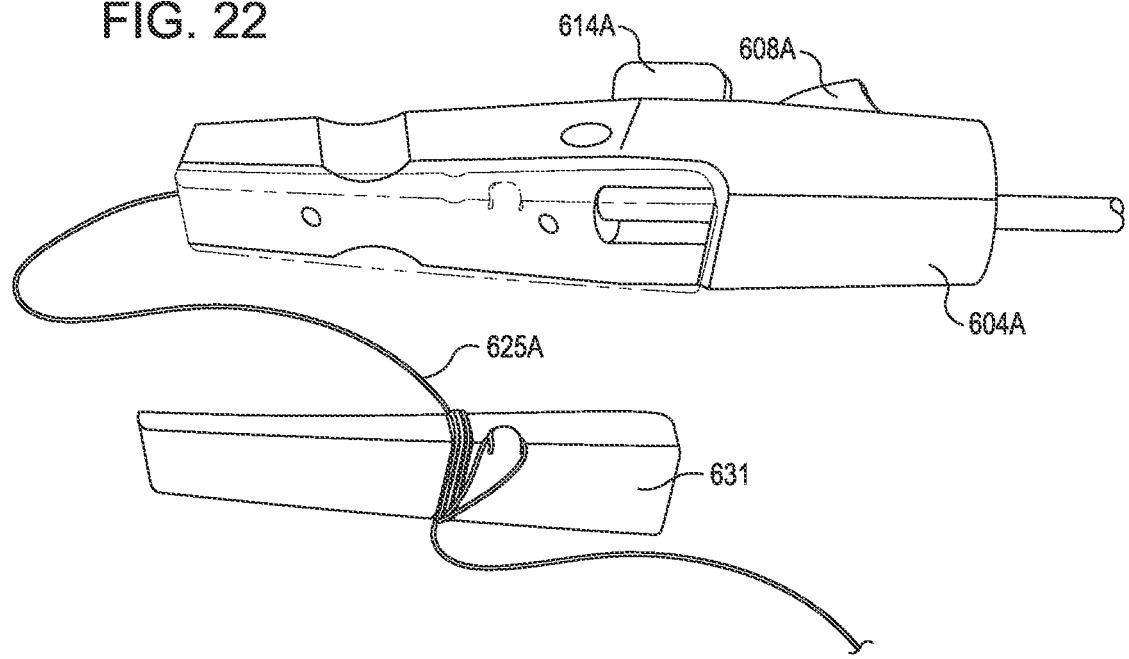
FIG. 22 is an exploded perspective view of a tissue repair delivery system with a paddle-type suture tensioning mechanism.

It is important to note that the sutures may also be tensioned by hand or with the use of some other tensioning mechanism. Tensioning sutures to a high force by hand can be difficult. As shown in FIG. 22, a simple paddle 631 may be attached to the suture strands 625A. The trigger 608A and the safety tab 614A are used as described above with FIG. 19. The paddle 631 in this embodiment may be attached to the side of the handle body 604A when not in use, After pulling the trigger 608 to expose the implant, the paddle 631 may be removed from the handle body and gripped to facilitate tensioning the sutures to adequately deploy the soft anchoring implant in the bone. The paddle 631 may be any rigid or semi-rigid material and may be of any shape that is readily grabbed by one's hand. In this embodiment, the suture strands 625A are passed through a hole in the center of the paddle 631 and wrapped multiple times around the paddle. If a specific distance of pull is required, marks on the suture may be utilized. Alternately an in-line breakaway tab may be incorporated which would break when a threshold tensile force is reached, thus assuring adequate tension on the suture. An example of such a break-away tab may be a bar of plastic that is attached in-line with the suture strand. Said bar may have a thinner and inherently weaker section within that is designed such that it will fracture or break when it reaches a give tensile load. A similar break-away tab may be incorporated into the paddle and may be the point of attachment for the suture strand.

Figure 23:
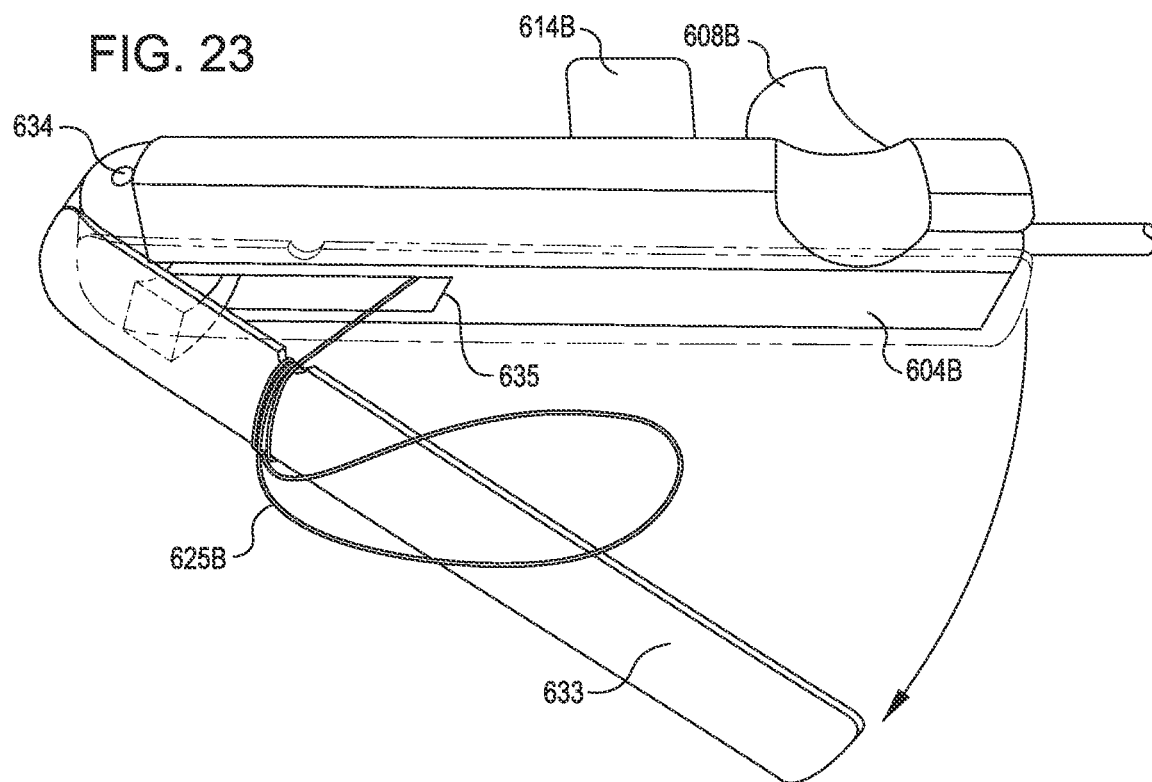
FIG. 23 is a perspective view of a tissue repair delivery system with a lever-type suture tensioning mechanism.

FIG. 23 shows another embodiment of an inserter design with a suture tensioning mechanism. The trigger 608B and the safety tab 614B are used as described above with FIG. 19. A lever-type mechanism is used here to tension the sutures 625B. The lever 633 is mounted on a hinge 634 at the proximal end of the handle body 604B which allows the lever 633 to be pulled away from the handle body 604B by its distal end. The suture strands 625B exit a hole 635 in the handle body 604B and pass through a hole in the lever 633 where they are wrapped around and tied, removing any slack. Following deployment of the implant by pulling the trigger 608B, the lever 633 is pulled, which in turn tensions the suture 625B. This is a useful mechanism as the lever 633 provides a mechanical advantage which will allow tensioning of the suture 625B to a high force. The rotation of the lever 633 can be limited a particular amount to provide the appropriate distance of pull on the implant, and/or a force limiter could be provided on the lever.

Figure 24:
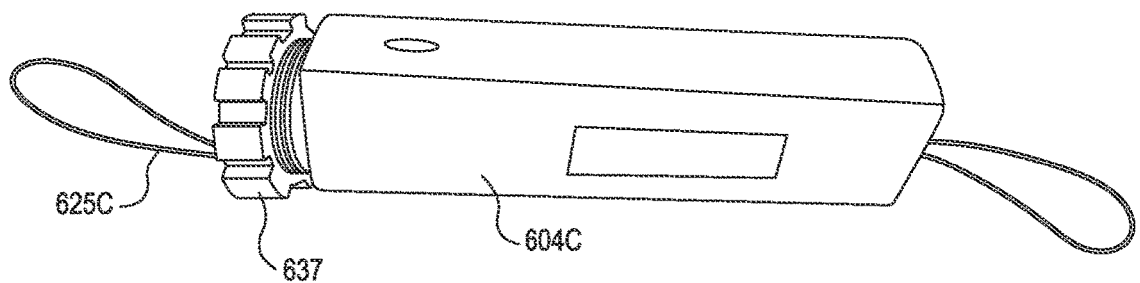
FIG. 24 is a perspective view of a tissue repair delivery system with a spool-type suture tensioning mechanism.

FIG. 24 shows another suture tensioning mechanism. The trigger (not shown) and the safety tab (also not shown) are used as described above with FIG. 19. A rotatable knob is 637 is mounted on the distal end of the handle body 604C. The suture strand(s) 625C are fed up through the handle body 604C, then through a slot in the outside of the rotatable knob 637 where it is knotted to prevent pull-through. Upon rotating the knob 637, the suture strand(s) is spooled around a groove in the outside of the knob 637, thereby tensioning the suture.

Figure 25:
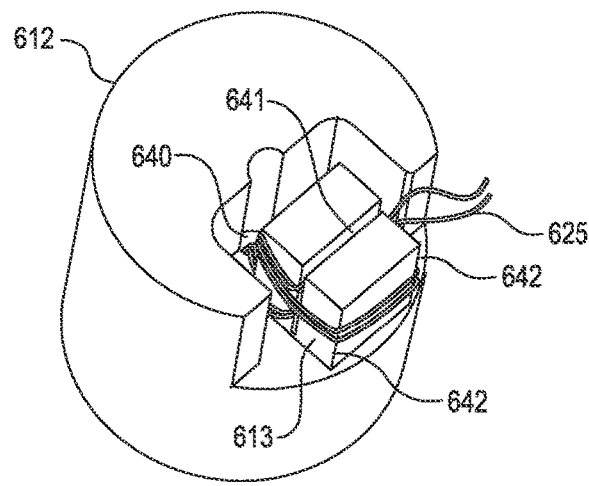
FIG. 25 is a perspective view of an embodiment of a suture retention disc with a suture post in accordance with embodiments.

FIG. 25 is an embodiment of a suture retention disc 612 with a suture post 613. The suture strands 625 exit the handle body and pass through a hole 640 in the suture retention disc 612. The suture strands are then wrapped around the post 613 one or more times before passing into a slot 641 within the suture post 613. The slot is configured to a width such that the suture strands are wedged between the two inner faces of the slot. Upon exiting the slot, the suture strands may be wrapped additional times around the post 613 and again through the slot 641. By wrapping around the post 613 before passing through the slot 641, a self-tightening feature is created. When tension is applied to the suture strands to expand the anchor, the portion of the strands that are wrapped around the post 613 apply a compressive force which effectively narrows the slot 641, creating a clamping force on the suture strand portion which runs through the slot, thus not allowing the suture to slip through the slot or around the post. This is important because it allows adequate tensioning of the sutures and thus adequate expansion and anchoring of the implant in the tissue.

In embodiments, the sharp corners 642, as opposed to a rounded configuration, may produce the effect of gripping the suture and preventing slippage.

Other embodiments of the suture retention posts include, but are not limited to, multiple posts on a single suture retention disc; multiple posts for attaching multiple sutures; posts directly attached to or integral with the knob shell or helix bushing or threaded knob; posts with multiple slots in various configuration, such as crossing slots; posts of various shapes including round, square rectangular, triangular, domed etc.

Figure 26:
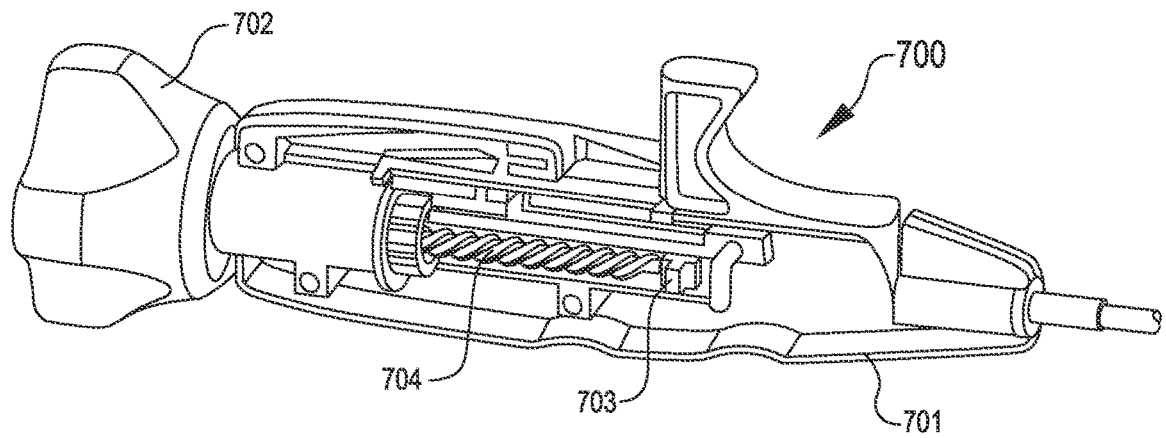
FIG. 26 is a partial section view of a tissue repair delivery system with an internal threaded shaft tensioning mechanism.

FIG. 26 is a partial cutaway perspective view of a tissue repair delivery system 700 with an internal threaded shaft tensioning mechanism. In this embodiment, a rotatable knob 702 is mounted on the back of the handle 701. A threaded piston 704 is mounted axially along the handle 701, and extends into the knob 702. The knob 702 includes internal female threads for receiving the threaded piston 704, which can be fixed so that it cannot rotate. The threaded piston may be fixed and prevented from rotation through the use of tabs 703 which extend orthogonal to the axis of the piston and slide within a slot defined on the inside surface of the handle. The suture strands (not shown) are attached to the threaded piston 704.

When the knob 702 is rotated, the threaded piston 704 moves proximally, pulling the suture strands with it. This movement tensions the suture strands. The amount of travel can be limited so as to provide the appropriate distance of pull and/or force on the suture strands.

Figure 27:
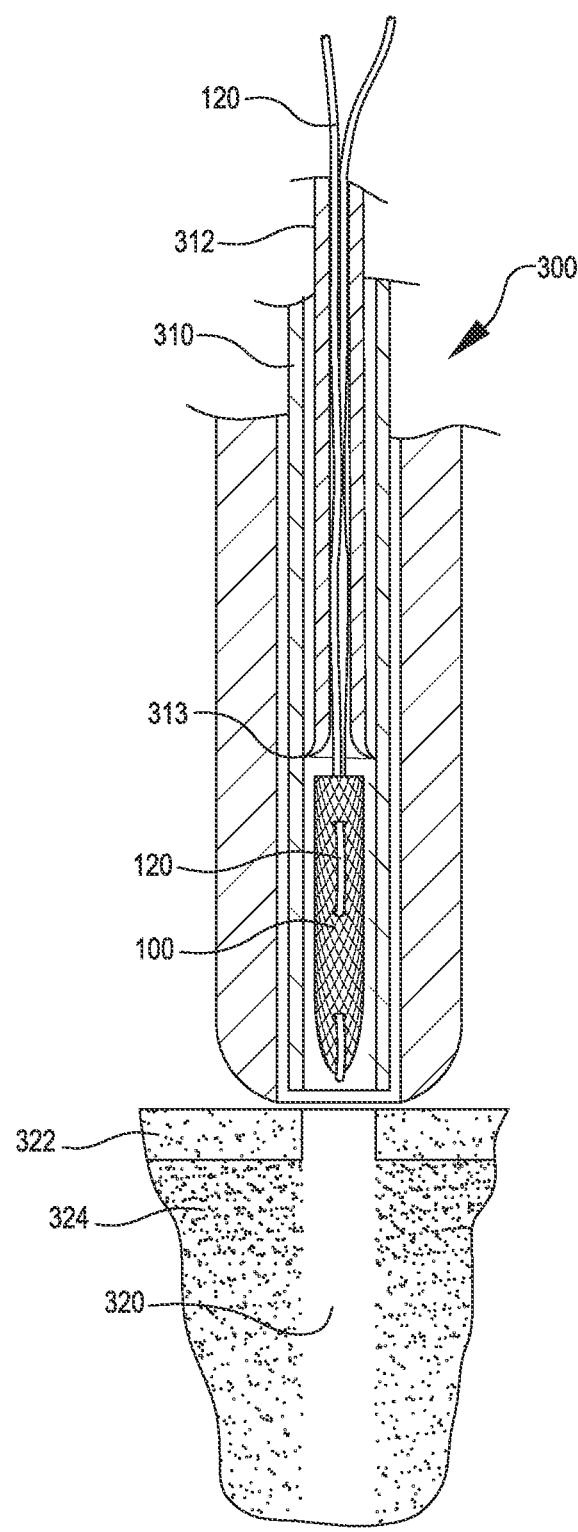
FIG. 27 is a section view showing the tissue repair system of FIG. 18 with flared implant pusher.

Turning to FIG. 27, a section view is shown of the tissue repair assembly 300. The fibers or yarns soft anchoring implant 100 is shown loaded into the inserter tube 310. The inserter tube is preferably metal and its diameter is generally the same as the diameter of a hole 320 that is drilled or otherwise formed in the cortical bone 322 and cancellous bone 324 into which the implant is to be inserted. A length of suture 120 is shown woven through the implant as described previously with the free ends of the suture exiting the open end of the soft anchoring implant and subsequently exiting the inserter tube 310 and the implant pusher 312. The implant pusher 312 is a preferably but not necessarily metal tube with an outer diameter generally the same as (or slightly smaller than) the outer diameter of the soft anchoring implant 100 and slightly smaller than the inner diameter of the inserter tube 310.

A close but slideable fit between the outer diameter of the implant pusher 312 and the inner diameter of the inserter tube 310 aids in preventing portions of the soft anchoring implant 100 from becoming wedged between the two tubes and provides generally better counter traction. In practice, however, a close fit between the outer diameter of the implant pusher 312 and the inner diameter of the inserter tube 310 may be hard to achieve. In this case, as in FIG. 27, the end of the implant pusher 312 may be configured to have a flare 313, Alternatively the end may be configured in any other manner, such as a bead, roll or additional component which will allow a closer fit to the inner diameter of the inserter tube or otherwise prevents pinching of the implant 100 between the inserter tube 310 and the implant pusher 312. The lumen of implant pusher 312 is of sufficient diameter as to allow the free passage of both ends of the suture 120. The inserter tube 310 with preloaded soft anchoring implant 100 and implant pusher 312 are shown inside the drill guide 314. The drill guide 314 is may be a metal tube with an inner diameter just large enough to allow the free passage of the inserter tube 310. It serves the dual purpose of guiding the drill for creating the hole in the bone as well as guiding the inserter tube 310.

When the tissue repair system is used in a bone anchoring scenario such as a rotator cuff repair or a labral repair, a hole 320 may be drilled into the bone where the soft anchoring implant is to be placed. This may be done using a standard orthopedic drill to a predetermined depth. The depth of the hole 320 is typically about the same as or slightly shorter than the length of the implant. As mentioned previously, the hole is drilled to a diameter roughly the same as the outer diameter of the soft anchoring implant. When drilling the hole, the drill guide 314 may be used with the drill placed through it. Upon removing the drill from the drill guide 314, the drill guide may be left in place and the inserter tube 310 with the preloaded soft anchoring implant is positioned in the drill guide as shown in FIG. 28, As shown in FIG. 29, the inserter tube 310 with soil anchoring implant housed inside may be pushed forward into the drilled hole 320. The implant pusher 312 also moves forward with the inserter tube 310 and remains close to or touching the proximal end of the implant.

Turning now to FIG. 30, another cross section view is provided showing the subsequent step to FIG. 29 in the use of the tissue repair system. The implant 100 is shown placed into the hole 320 in a coaxial orientation. This is done by retracting the inserter tube 310 in an axial direction while the implant pusher 312 remains in place. The implant pusher 312 is preferably connected on the proximal end to the handle which is not moveable, while the inserter tube 310 is attached at its proximal end to an activation knob, slide, or trigger (e.g., the trigger 608) housed within a handle which can be activated by the user. Once the inserter tube 310 has been retracted to the outermost level of the bone, the implant is left inside the preformed hole, exposed to the bone as shown in FIG. 30.

At this point, the sutures may be tensioned as shown in FIG. 31, with the implant pusher 312 remaining stationary within the bone space. The implant pusher 312 ideally extends into the bone to the bottom of the cortical layer, typically 0.02" to 0.05" below the bone/tissue surface. As the sutures 120 are tensioned, the implant 100 retracts upon itself with the end of the implant pusher 312 providing counter traction and assumes a shorted, expanded state with an increased effective diameter. By "counter traction," we mean a back stop is provided resisting movement of the proximal end of the implant proximally, thus causing the implant to bunch and expand.

Expansion is accomplished primarily by the orientation change of the fibers as discussed earlier. When the implant 100 increases in diameter, the soft anchoring implant becomes larger than the hole through which it was inserted in the cortical bone 322, thus resisting pull out. The soft anchoring implant 100 also embeds itself to some degree into the cancellous bone 324 that makes up the majority of the walls of the hole 320. This is possible because in most cases, the cancellous bone 324 is significantly softer than the associated cortical bone layer 322 above it. This "embedding" of the implant into the cancellous bone may also contribute to resistance of the implant to pull out. The soft anchoring implant 100 is preferably placed into the bone in a lengthwise or axial orientation, such that one of the ends (the closed end or the open end) enters the bone first, with the opposite end entering last. In the embodiment of an implant with two closed ends, the end with the suture length 120 encircling the distal end is preferably placed into the hole first.

In an alternative embodiment, the hole 320 may be sized such that it will not accept the inserter tube 310. In this embodiment, the inserter tube 310 with the preloaded soft anchoring implant 100 is stopped at the entrance of the bone hole and a moveable implant pusher may be used to push the implant to the bottom of the hole 320. A stop mechanism may also be used here to prevent movement of the implant pusher 312 too far into the hole 320.

In a related embodiment of tissue repair system, a partial hole may be drilled or punched. This hole may breach the cortical bone layer, yet not penetrate the softer cancellous bone. The inserter tube may be configured with a temporarily closed end such that it may be forced by pushing or malleting so as to penetrate the cancellous bone and place the implant at the desired depth. Alternatively, such a configured tissue repair system may be used to penetrate the cortical bone as well.

Figure 32:
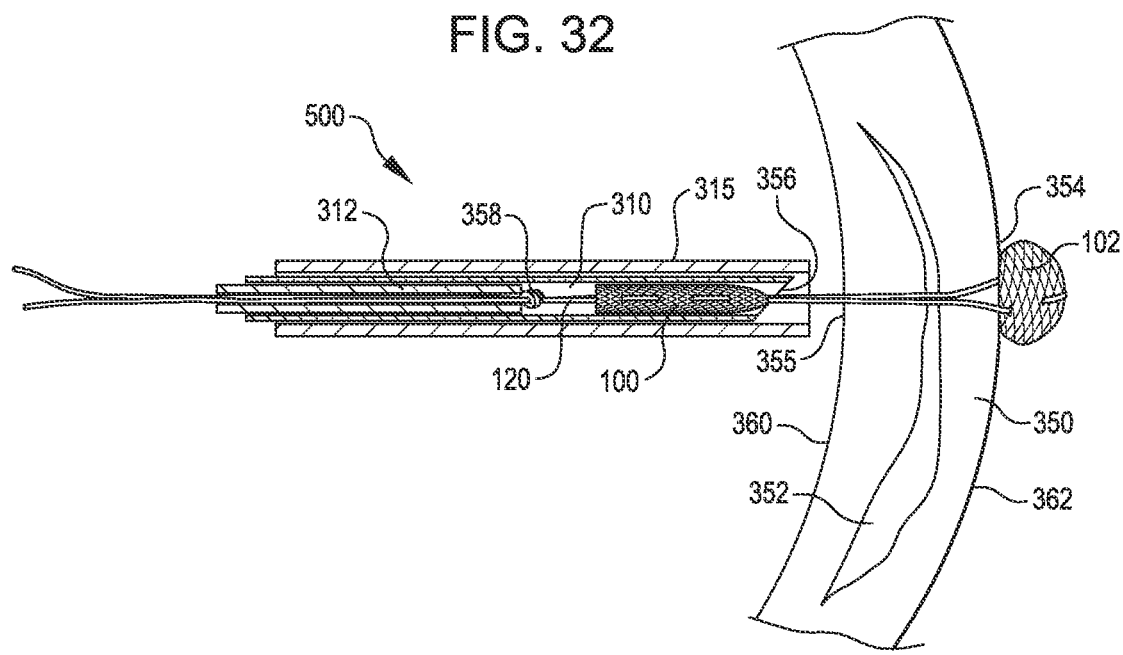
FIG. 32 is a section view of an embodiment of the tissue repair system as used to repair a defect in soft tissue.

Turning now to FIG. 32, a tissue repair system is shown which may be used to repair defects in soft tissue or attach two separate pieces of soft tissue. The soft anchoring implant may be substantially the same as previously disclosed herein. In the figure, a section of tissue 350 is shown with a tear or defect 352 that requires surgical repair and a tissue repair assembly 500 which is configured with two soft anchoring implants 100 and 102 (shown deployed). These implants may be of similar size and configuration as previously disclosed herein. In the figure, the first soft anchoring implant 102 is shown already deployed against a section of tissue 354 distal to the tissue repair assembly 500. The sharp edge 356 of the inserter tube 310 is used to penetrate the tissue and the defect, emerging on the distal side of the tissue 354. The soft anchoring implant is pushed out of the inserter tube 310 by the implant pusher 312 and deployed by tensioning the suture 120, Tensioning the suture pulls the implant against the tissue 354 which provides counter traction, thus allowing the implant to compress axially and expand radially as previously described.

A second soft anchoring implant 100 is shown still residing in the inserter tube 310 with the trailing suture 120 from the deployed implant 102 passing through it. The suture 120 exits the open end of the implant as previously described, A sliding knot 358 is located within the inserter tube 310 behind the second implant 100. The implant pusher 312 is used to push the sliding knot and the second implant 100 from the inserter tube 310. After tensioning the suture to deploy the second implant against a proximal portion of the tissue 355, the implant pusher 312 is advanced to position the sliding knot against the deployed implant. The suture 120 may then be trimmed to complete repair, A guide tube 315 may be used to position the inserter tube 310 against the tissue.

In an alternative embodiment, a jump stitch or mattress stitch may be created by penetrating the tissue a second time at an adjacent location 360 and deploying the second implant 100 at a second distal tissue location 362. The inserter tube may be configured with a slot at the distal end to facilitate this technique by allowing the suture strand to remain on the proximal side of the tissue during the second penetration.

Figure 33:
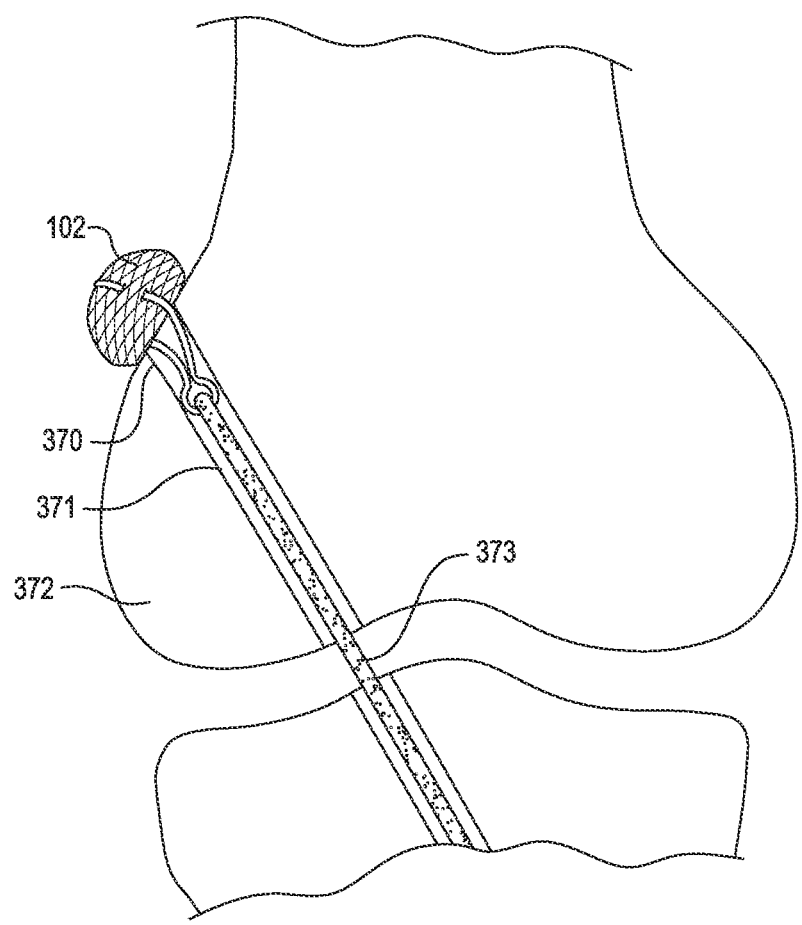
FIG. 33 is a section view of an embodiment of the tissue repair system as used as a retention anchor on the outside surface of a bone.

FIG. 33 shows a tissue repair system used as a retention anchor on the outside of a hone as might be done in attaching a graft ligament in an ACL repair. In this embodiment, a soft anchoring member 102 is shown in a deployed state outside the distal end 370 of channel 371 bored through the bone 372. A similar tissue repair system configuration may be used to deploy the soft anchoring implant 102 as has been disclosed in previous embodiments. In this embodiment a tissue graft 373 may be pre-attached to the suture 120 associated with the soft anchoring implant 102. In this embodiment, the soft anchoring implant 102 may preferably be sized such that its diameter is inherently larger than the hole through which it is placed, thus providing better retention properties. Because of the flexible nature of the implant 102, it may be folded or compressed to fit into the inserter tube that is smaller than its inherent diameter as in all other embodiments disclosed herein.

Figure 34:
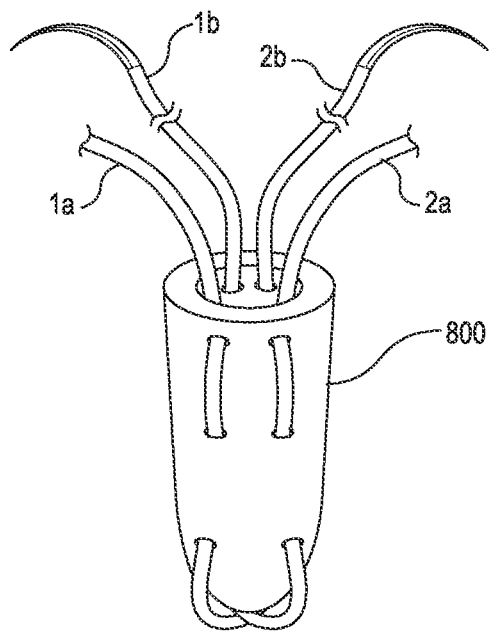
FIG. 34 is a perspective view of an implant in accordance with embodiments.

FIG. 34 shows another embodiment of a soft anchoring implant 800 which may be used for attaching a tendon to a bone. In this embodiment two suture strands are communicated with the implant. The ends (1b and 2b) of the suture strands are configured with needles.

Figure 35:
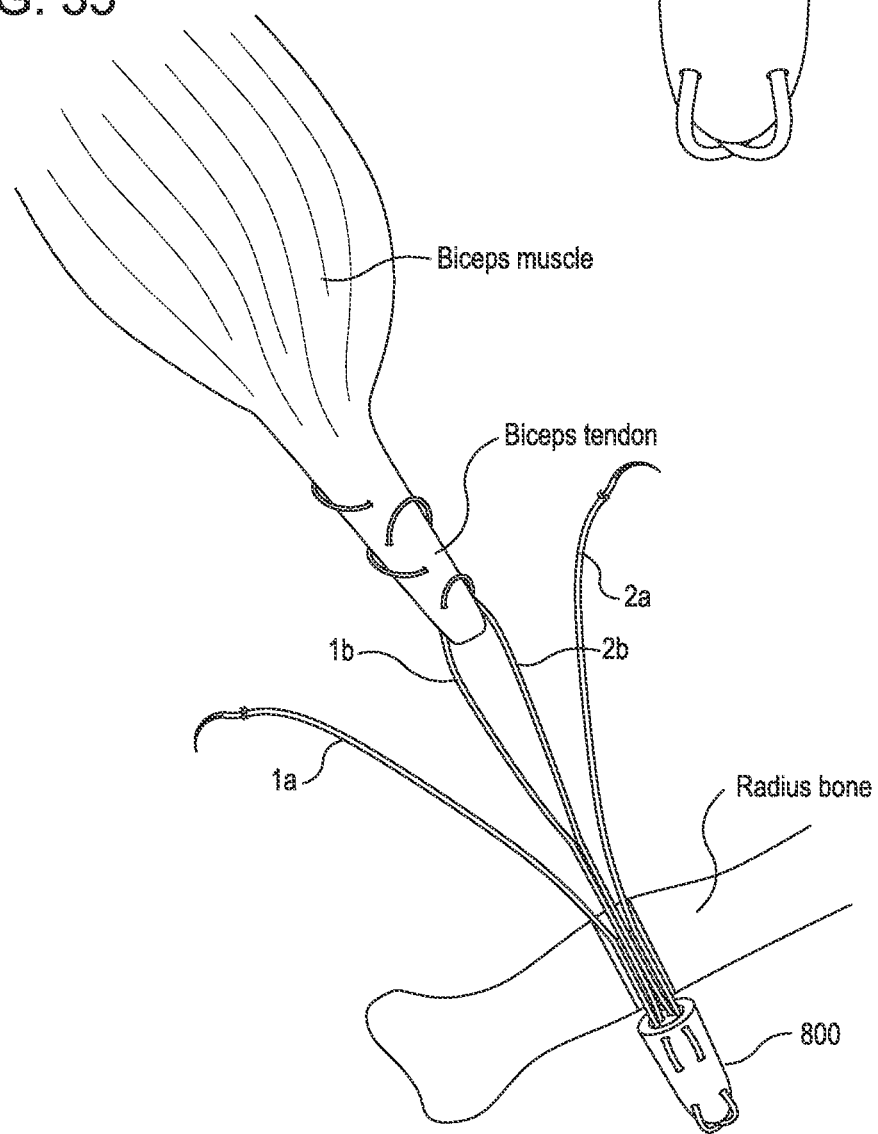
FIG. 35 is a representation of installation of the implant of FIG. 34 into a Weep accordance with embodiments.

FIG. 35 shows the biceps muscle and associated biceps tendon. The needles (1b and 2b) are passes through the biceps tendon in a crossing or whipstitch fashion to permanently connect the suture to the tendon. A hole is drilled through the radial bone and the soft anchoring implant 800 is passed all the way through the bone and deployed on the opposite side of the bone. The suture strands (1a and 2a) are then tensioned to approximate the biceps tendon to the bone and into the drilled hole. Tensioning the sutures (1a and 2a) also produces the effect of further expanding the soft anchoring implant 800 on the opposite side of the bone to provide better retention. The suture ends are then trimmed and tied off.

In another embodiment, a tunnel may be created through adjacent bones, with the inserter being passed through both bones in a similar fashion to FIG. 35

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An anchor assembly for securing tissue to a bone or tissue to tissue, comprising:
   a soft anchoring implant for inserting into a tunnel in bone or tissue of an animal or human, the soft anchoring implant defining a tube terminating at a bound distal end, the bound distal end comprising a linear edge, wherein the bound distal end is at least partially closed with an adhesive or by heat sealing; and
   a suture, interwoven along the soft anchoring implant; and wherein tensioning a first and second end of the suture when the soft anchoring implant is installed in a tunnel in bone or through the tissue of an animal or a human, causes the soft anchoring implant to change from a first configuration where the tube of soft anchoring implant is elongate into a second configuration where the tube is compressed axially and extended radially so as to form an anchor in the tunnel.

2. The anchor assembly of claim 1, wherein the soft anchoring implant comprises a biaxial braid.

3. The anchor assembly of claim 1, wherein the suture extends substantially parallel along a longitudinal axis of the soft anchoring implant, over the linear edge, and returns substantially parallel to the longitudinal axis along an opposite side of the soft anchoring implant, with the first and second ends of the suture exiting adjacent a proximal end of the soft anchoring implant.

4. The anchor assembly of claim 1, wherein the soft anchoring implant is configured to compress radially and extend axially relative to the first and second configuration so as to fit within an inserter tube of an inserter device.

5. The anchor assembly of claim 1 wherein in the second configuration the tube is compressed axially and extended radially to be configured to at least partially embed within walls of the tunnel.

6. The anchor assembly of claim 1 wherein the soft anchoring implant defines a non-zero resident volume when in the first configuration and substantially no resident volume when in the second configuration.

7. The anchor assembly of claim 1 wherein the tunnel in the bone or tissue defines a first diameter and in the second configuration the soft anchoring implant is extended radially to be configured to enlarge the first diameter adjacent the soft anchoring implant.

8. An anchor assembly for securing tissue to a bone or tissue to tissue, comprising:
   a flexible tubular implant having a distal end that is bound closed defining a distal linear edge and wherein the distal end is at least partially bound closed with an adhesive or a heat sealed end; and
   a length of suture having two ends, the length of suture extending through the flexible tubular implant, and wherein tensioning at least one suture end while providing some counter traction, causes the flexible tubular implant to change from a first configuration where the flexible tubular implant is elongate into a second configuration where the flexible tubular implant is compressed axially and extended radially.

9. The anchor assembly of claim 8, wherein the length of suture extends parallel to a longitudinal axis of the flexible tubular implant and through a portion of a sidewall of the flexible tubular implant towards the distal end, and also extends parallel to the longitudinal axis and through a portion of the sidewall on an opposing side of the longitudinal axis, both suture ends exiting adjacent a proximal end of the flexible tubular implant.

10. The anchor assembly of claim 8 wherein a longitudinal axis of the flexible tubular implant is in the same orientation in both the first and second configuration, said orientation parallel to a longitudinal axis of a tunnel formed within the bone or tissue for receiving the flexible tubular implant therein.

11. The anchor assembly of claim 8 wherein the flexible tubular implant is formed from braided threads.

12. The anchor assembly of claim 11, wherein a portion of the length of suture extends between the braided threads.

13. The anchor assembly of claim 11, wherein the braided threads are aligned more parallel with each other in the first configuration and aligned so as to be less parallel in the second configuration.

14. The anchor assembly of claim 8 wherein in the second configuration the flexible tubular implant is compressed axially and extended radially to be configured to at least partially embed within walls of the bone or tissue.

15. The anchor assembly of claim 8 wherein the flexible tubular implant defines a non-zero resident volume when in the first configuration and substantially reduced resident volume when in the second configuration.

16. An anchor assembly for securing tissue to a bone or tissue to tissue, comprising:
   a soft anchoring implant comprising braided threads forming a tube with a longitudinal axis and sidewalls, the braided threads terminating at a bound distal end comprising a linear edge, wherein the bound distal end is at least partially closed with an adhesive or by heat sealing; and a suture connected to the soft anchoring implant;
   wherein tensioning a first and second end of the suture causes the soft anchoring implant to change from a first configuration that is elongate to a second configuration that is expanded and configured to wedge within the bone or tissue.

17. The anchor assembly of claim 16, wherein the braided threads are configured in the first configuration so that applying tension to only one end of the suture without counter traction allows the suture to slide through the soft anchoring implant without changing the soft anchoring implant to the second configuration.

18. The anchor assembly of claim 16, wherein the braided threads form a biaxial braid that is aligned more parallel to the longitudinal axis in the first configuration and aligned so as to be less parallel in the second configuration.

19. The anchor assembly of claim 16 wherein the tube defines a non-zero resident volume when in the first configuration and substantially no resident volume when in the second configuration.

20. The anchor assembly of claim 16 wherein the soft anchoring implant has a third configuration, wherein the soft anchoring implant is radially reduced relative to both the first and second configuration, sufficient to fit within an inserter cavity of an inserter instrument.

\* \* \* \* \*